United States Patent
Shaimi

(10) Patent No.: US 8,182,236 B2
(45) Date of Patent: May 22, 2012

(54) PROCESS AND DEVICE FOR THE HIGH-PRESSURE DELIVERY OF A FLUID MIXTURE AND USE OF SAME

(75) Inventor: Mohamed Shaimi, Montfavet (FR)

(73) Assignee: PIC Solution, Avignon (FR)

( * ) Notice: Subject to any disclaimer, the term of this patent is extended or adjusted under 35 U.S.C. 154(b) by 919 days.

(21) Appl. No.: 11/884,997

(22) PCT Filed: Feb. 22, 2006

(86) PCT No.: PCT/FR2006/000402
§ 371 (c)(1),
(2), (4) Date: Sep. 15, 2008

(87) PCT Pub. No.: WO2006/090063
PCT Pub. Date: Aug. 31, 2006

(65) Prior Publication Data
US 2009/0175738 A1 Jul. 9, 2009

(30) Foreign Application Priority Data
Feb. 25, 2005 (FR) ..................... 05 01961

(51) Int. Cl.
*F04B 25/00* (2006.01)
*F04B 23/08* (2006.01)

(52) U.S. Cl. ....... 417/53; 417/452; 417/504; 222/145.5; 222/145.6; 222/135; 222/132

(58) Field of Classification Search .................. 417/53, 417/452, 504; 222/145.5–145.6, 135, 132
See application file for complete search history.

(56) References Cited

U.S. PATENT DOCUMENTS

| | | |
|---|---|---|
| 4,311,586 A | 1/1982 | Baldwin et al. |
| 5,196,575 A | 3/1993 | Sebastien et al. |
| 5,198,115 A | 3/1993 | Stalling et al. |
| 6,743,356 B1 | 6/2004 | Fermier et al. |
| 2002/0144949 A1 | 10/2002 | Berger et al. |
| 2004/0018099 A1 | 1/2004 | Berger et al. |

FOREIGN PATENT DOCUMENTS

DE  196 25 648  1/1997

*Primary Examiner* — Tracie Y Green
(74) *Attorney, Agent, or Firm* — Bachman & LaPointe, P.C.

(57) ABSTRACT

A method for the high-pressure delivery of a mixture comprises delivering at least first and second fluids. The method comprises operations consisting in forming a mixture of fluids in a mixing zone having a pressure that is less than the desired high pressure and bringing the pre-mixed fluids to the high pressure. The first fluid is introduced into the mixing zone by a pumping operation that is performed by a high-pressure pump that is positioned downstream of the mixing zone. A device for performing the method is described.

10 Claims, 1 Drawing Sheet

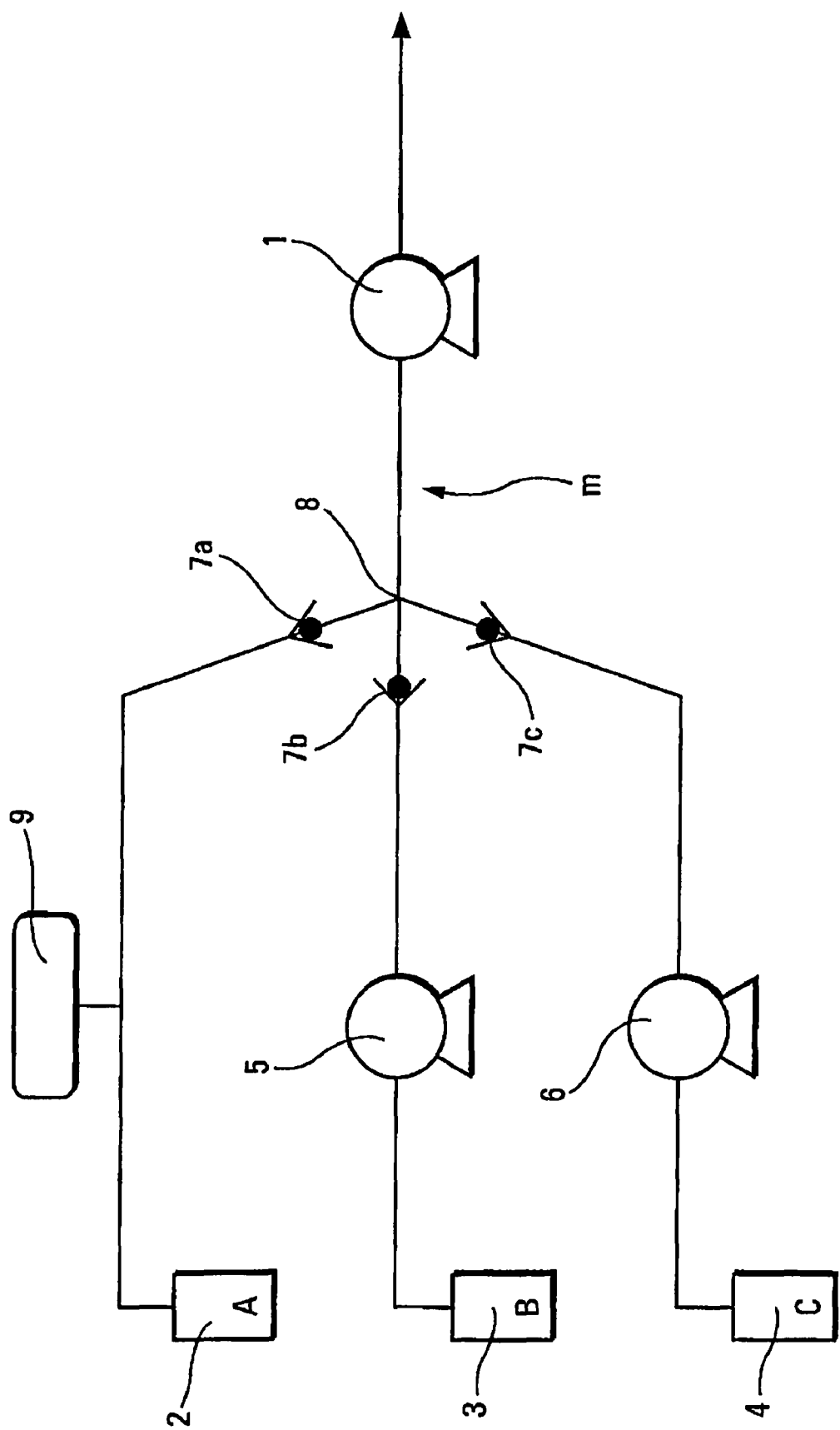

PROCESS AND DEVICE FOR THE HIGH-PRESSURE DELIVERY OF A FLUID MIXTURE AND USE OF SAME

The present invention relates to the general field of circulation and of supplying fluids and, in particular, providing mixture of fluids at high pressure.

More precisely, the invention relates to, according to a first of its aspects, a process for high pressure delivery of a mixture of at least a first and second fluid, this process comprising the operations consisting of forming a mixture of fluids in a mixing zone in which a pressure less than the high pressure prevails, and bringing the previously mixed fluids to high pressure.

Currently, to carry out high-pressure mixing of several fluids, it is current to use as many high-pressure pumps as fluids, the mixing being completed downstream of the pumps. This system adjusts the percentages of the different fluids in the final mixture, but using several high-pressure pumps makes the process costly.

In U.S. Pat. No. 4,311,586, mixing three solvents is done by mounting the high-pressure pump downstream of three low-pressure pumps mounted in parallel and each receiving one of the three solvents. However, this installation requires as many low-pressure pumps as solvents.

The aim of the present invention is therefore to propose an improved process for providing mixing of fluids at high pressure.

For this purpose, the process of the invention, also in keeping with the generic definition, the preamble of which is given hereinabove, is essentially characterised in that the first fluid is admitted to the mixing zone by a pumping procedure carried out by a high-pressure pump placed downstream of said mixing zone (m).

According to an advantageous version of the invention, the first fluid is pumped from a container in which it is subjected to a pressure greater than those prevailing inside the containers containing respectively each second fluid.

In another embodiment of the invention, the first fluid is pumped from a container in which it is subjected to a pressure equal to those prevailing inside the containers containing respectively each second fluid, and in that each second fluid undergoes counter-pressure prior to arriving in the mixing zone.

According to a particular embodiment of the invention, the first fluid is any solvent able to be utilized in chromatography in supercritical phase, such as carbon dioxide, and the second fluid is a modifying agent.

Modifying agent is understood to mean a co-solvent of the first fluid, which is made up of liquid solvent or a mixture of liquid solvents.

By way of advantage, the high pressure is between 30 and 300 bars, preferably between 100 and 300 bars, and the pressure less than the high pressure is between 1 and 100 bars and, preferably, is of the order of 50 bars.

The invention also relates to a device utilising a single high-pressure pump to deliver at its outlet a mixture of at least a first and second fluid, each second fluid being delivered to the inlet of said high-pressure pump each by a low-pressure pump having a return pressure less than the return pressure of the high-pressure pump, characterised in that each first fluid is pumped by the high-pressure pump.

The invention thus has the advantage of reducing operating costs for a device for high-pressure delivery of a mixture of fluids by limiting the number of necessary pumping devices.

Therefore, the device according to the invention offers good reproducibility of the flow of the second fluid, since the low-pressure pump functions at constant return pressure, which is the aspiration pressure of the high-pressure pump.

Each first fluid is preferably pumped from a container in which it is subjected to a pressure greater than those prevailing inside the containers containing respectively each second fluid.

It is possible also for each first fluid to be pumped from a container in which it is subjected to a pressure equal to those prevailing inside the containers containing respectively each second fluid, and that a calibrated valve or a counter-pressure device is installed downstream of each low-pressure pump, upstream of a node where the fluids to be mixed are combined.

According to an advantageous version of the invention, the high-pressure pump has a return pressure of between 30 and 300 bars, preferably between 100 and 300 bars, and each low-pressure pump has a return pressure of between 1 and 100 bars, preferably of the order of 50 bars.

The invention further relates to the application of the process according to the invention to chromatography in supercritical phase, extraction with a supercritical fluid or to liquid chromatography.

In these application examples of the process according to the invention, mixing the solvents is performed and delivered according to the invention and constitutes the mobile phase of chromatography.

Other advantages and particular features of the invention will emerge from the following detailed description, by way of indication and non-limiting, in reference to FIG. 1 which schematically illustrates a device for carrying out the process according to the invention in the case of mixing three fluids.

A high-pressure pump 1 receives three fluids A, B and C mixed upstream of the high-pressure pump 1 in the mixing zone m.

A first fluid A is kept under a set pressure in an container 2. It is directly removed from this container by pumping from the high-pressure pump 1. The flow rate at the outlet of the container 2 depends on the aspiration pressure of the high-pressure pump 1.

Two other fluids B and C are each removed from a container 3, 4 by pumping with a low-pressure pump 5, 6.

In this way, the process according to the invention has the advantage of eliminating, for mixing three fluids, the need for three low-pressure pumps. Two suffice.

Anti-return valves 7a, 7b, 7c can also be installed for each fluid upstream of the node 8 where the three fluids A, B and C are mixed.

According to a preferred embodiment, the pressure $P_A$ which the fluid A in the container 2 is under is greater than the pressures $P_B$ and $P_C$ to which the second fluids B and C in their respective containers 3 and 4 are subjected.

If $P_A$ is equal to $P_B$ and/or $P_C$, to prevent the high-pressure pump 1 from pumping the fluids A, B and/or C at the same time, a counter-pressure must be exerted downstream of the pumps 5 and/or 6 and upstream of the node 8. It can thus be ensured that the valves 7b and/or 7c are calibrated valves.

If preferred, another measuring device 9 of the rate at the outlet of the container 2 containing the first fluid A can be added, to ensure proper regulating of the pumping device and, if required, to modify this regulating.

Such a modification can relate to the high-pressure pump 1. For example, the measuring device 9 can be connected to the high-pressure pump 1 and the regulating thereof can be done automatically by computer of the regulation loop type by identification of the parameters (PAD).

By way of advantage, a pulse damper can be installed between the valve 7a and the node 8 to dampen the pressure shocks emanating from interruption closure of the high-pressure pump 1. The process according to the invention can be used in particular in chromatography for mixing several solvents. For example, a chromatography process in supercritical phase is utilized here.

There can be a need in this case to mix a first fluid A with a second fluid B, respectively a solvent and a co-solvent or modifying agent. The solvent is any fluid able to be used in chromatography in supercritical phase, such as carbon dioxide $CO_2$.

For example, $CO_2$ is at a pressure of 50 bars in the container 2 and the pump 5 for the co-solvent is at a return pressure equal to the pressure to which the container 2 is subjected.

With the process according to the invention, improved reproducibility of the pumping rate of the modifier is obtained, since the return pressure of the modifier pump is constant. With this improvement, the pump for the solvent also serves as solvent-modifier mixing chamber. In addition, the yield of the solvent pump, or of the high-pressure pump 1, is improved, as the fluid entering the pump contains a liquid co-solvent and is thus less compressible.

The process according to the invention can be useful in extraction with a supercritical fluid. Supercritical fluid means any fluid capable, in certain temperature and pressure conditions, of being in the supercritical state.

As in chromatography in supercritical phase, extraction with a supercritical fluid uses a solvent such as carbon dioxide $CO_2$ and a co-solvent acting as modifying agent. This solvent and co-solvent can advantageously be mixed by high-pressure pumping according to the process of the invention.

In liquid chromatography, there can be a need for mixing two solvents. The mixture can be made in isocratic mode or in gradient mode. For example, a liquid solvent is in the container 2 at a pressure of the order of 3 bars and the low-pressure pump 5 for the co-solvent functions at a return pressure equal to the pressure to which the container 2 is subjected, or a return pressure of the order of 3 bars.

The process according to the invention can even be utilized in any application requiring a pumping device for mixing several fluids and delivering the resulting mixture.

Implementing the process according to the invention constitutes means of diminishing the costs generated by the setting up a classic pumping device to deliver a mixture of fluids.

The invention claimed is:

1. A process for delivery of a mixture of at least a first and a second fluid at a high pressure between 30 and 300 bars, said first fluid being supplied to a mixing zone at a supply pressure above atmospheric but less than said high pressure, said process comprising the steps of forming a mixture of the first and second fluids in said mixing zone in which a pressure is determined by the supply pressure of the first fluid into the mixing zone and of bringing the mixed first and second fluids to said high pressure, and said forming step comprising admitting said first fluid to the mixing zone by a pumping procedure performed by a high-pressure pump placed downstream of said mixing zone.

2. The process as claimed in claim 1, further comprising pumping the first fluid from a container in which the first fluid is subjected to a pressure greater than at least one pressure which prevails inside at least one container containing said second fluid.

3. The process as claimed in claim 1, further comprising pumping the first fluid from a container in which the first fluid is subjected to a pressure equal to at least one pressure which prevails in at least one container containing said second fluid, and said second fluid undergoing counter-pressure before arriving in the mixing zone.

4. The process as claimed in claim 1, wherein the first fluid is any solvent able to be utilized in chromatography in supercritical phase, and the second fluid is a modifying agent.

5. The process as claimed in claim 1, wherein the pressure less than the high pressure is between 1 and 100 bars.

6. The process as claimed in claim 5, wherein the high pressure is between 100 and 300 bars and the pressure less than the high pressure is of the order of 50 bars.

7. The process as claimed in claim 1, further comprising applying said process to chromatography in supercritical phase or to extraction with a supercritical fluid.

8. The process as claimed in claim 1, further comprising applying said process to liquid chromatography.

9. A process for delivery of a mixture of a first fluid and two second fluids, said process comprising the steps of forming a mixture of the first and second fluids in a mixing zone in which a pressure between 1 and 100 bars prevails, said mixture forming step comprising admitting said first fluid to the mixing zone by a pumping procedure performed by a high-pressure pump placed downstream of said mixing zone, and bringing the mixed first and second fluid to a pressure between 30 and 300 bars.

10. The process as claimed in claim 9, further comprising pumping the first fluid from a container in which the first fluid is subjected to a pressure greater than pressures which prevail inside containers containing the two second fluids.

\* \* \* \* \*